(12) United States Patent
Yoshida et al.

(10) Patent No.: US 12,179,665 B2
(45) Date of Patent: Dec. 31, 2024

(54) DRIVER STATE DETERMINATION APPARATUS

(71) Applicant: MAZDA MOTOR CORPORATION, Hiroshima (JP)

(72) Inventors: Wataru Yoshida, Hiroshima (JP); Akira Kaino, Hiroshima (JP)

(73) Assignee: MAZDA MOTOR CORPORATION, Hiroshima (JP)

( * ) Notice: Subject to any disclaimer, the term of this patent is extended or adjusted under 35 U.S.C. 154(b) by 146 days.

(21) Appl. No.: 18/189,809

(22) Filed: Mar. 24, 2023

(65) Prior Publication Data

US 2023/0382298 A1 Nov. 30, 2023

(30) Foreign Application Priority Data

May 30, 2022 (JP) ................................. 2022-087595

(51) Int. Cl.
*B60Q 9/00* (2006.01)
(52) U.S. Cl.
CPC ...................... *B60Q 9/00* (2013.01)
(58) Field of Classification Search
CPC ........................................................ B60Q 9/00
USPC .......................................................... 340/439
See application file for complete search history.

(56) References Cited

U.S. PATENT DOCUMENTS

| | | | | |
|---|---|---|---|---|
| 2009/0273458 | A1* | 11/2009 | Almqvist | A61B 5/18 340/439 |
| 2011/0035100 | A1* | 2/2011 | Sanma | B60K 35/00 701/36 |
| 2019/0193754 | A1* | 6/2019 | Augst | B60Q 9/00 |

FOREIGN PATENT DOCUMENTS

| | | |
|---|---|---|
| JP | 2017-144808 A | 8/2017 |
| JP | 6455456 B2 | 1/2019 |
| JP | 2021-077136 A | 5/2021 |

* cited by examiner

*Primary Examiner* — Naomi J Small
(74) *Attorney, Agent, or Firm* — Studebaker & Brackett PC

(57) ABSTRACT

A driver state determination apparatus detects the decline of the physical function of a driver and confirms the determination of an abnormal state before the driver becomes unable to drive. A vibration apparatus vibrates a steering wheel; a vibration detector detects the vibration of the steering wheel; and a controller controls the vibration apparatus. The controller provides vibration at a predetermined excitation frequency to the steering wheel by the vibration apparatus, calculates a steering torque level at the excitation frequency based on the vibration detected by the vibration detector, and determines that a driver is in an abnormal state when an average value of the steering torque level while the vibration is being provided is equal to or more than a first threshold value, and/or a standard deviation of the steering torque level while the vibration is being provided is equal to or more than a second threshold value.

12 Claims, 4 Drawing Sheets

DRIVER STATE DETERMINATION APPARATUS

TECHNICAL FIELD

The present disclosure relates to a driver state determination apparatus for determining whether a driver is in an abnormal state while a vehicle is being driven.

BACKGROUND

Hitherto, an apparatus that issues a warning to a driver by sound and a lamp when it is determined that a driver is in an abnormal state has been proposed (for example, see Japanese Patent No. 6455456). In the apparatus described in Japanese Patent No. 6455456, a warning is generated toward the driver when a state in which there are no operation inputs by the driver continues for a predetermined amount of time (for example, 5 seconds) while a vehicle is traveling by an autonomous driving assistance mode (for example, lane keeping assistance). Then, when the amount of time without an operation input by the driver further continues, warning and autonomous intervention (deceleration and the like) to vehicle operation are sequentially performed.

SUMMARY

It is known that the decline in function of the human body gradually progresses from a high-order function to a low-order function when some sort of disease (for example, heart disease, brain disease, or hypoglycemia) initiates. For example, the decline in function of voluntary movement (in other words, a high-order function) gradually progresses over several tens of minutes until movement cannot be performed. Then, the driver becomes unable to perform driving operation within several seconds from the occurrence of the decline in function of involuntary movement (in other words, a low-order function). Here, during the decline in function of the voluntary movement, a lane keeping ability and a speed keeping ability of the driver, for example, decline as compared to when the driver is healthy, but the driver is able to perform the vehicle operation although the vehicle operation is imperfect. Therefore, in the related-art apparatus that determines that the driver is in an abnormal state when the driver becomes unable to perform operation, the determination of an abnormal state cannot be performed during the decline in function of the voluntary movement.

Meanwhile, when the decline in function of involuntary movement occurs, the driver becomes unable to perform operation within several seconds. Therefore, there may be little time from the determination of an abnormal state to the confirmation of the driver's will or the execution of an appropriate action such as autonomous stopping of the vehicle. Therefore, it is desired that it be possible to determine that the driver is in an abnormal state at high accuracy in a stage before the decline in function of involuntary movement occurs, in other words, a stage in which the decline in function of voluntary movement is occurring.

The present disclosure has been made in order to solve such a problem by providing a driver state determination apparatus capable of detecting the decline of the physical function of a driver and confirming the determination of an abnormal state early; that is, before the driver becomes unable to drive.

In order to solve the problem described above, the present disclosure provides a driver state determination apparatus that determines an abnormal state of a driver that drives a vehicle, the driver state determination apparatus including a vibration apparatus that vibrates a steering wheel of a steering apparatus of the vehicle; a vibration detector that detects the vibration of the steering wheel; and a controller that controls the vibration apparatus. In the driver state determination apparatus, the controller is configured to provide vibration at a predetermined excitation frequency to the steering wheel by the vibration apparatus, calculate, based on the vibration detected by the vibration detector, a value indicating a strength of the detected vibration at the excitation frequency, and determine that the driver is in an abnormal state when an average value of the value indicating the strength of the vibration while the vibration is being provided is equal to or more than a first threshold value, and/or a standard deviation of the value indicating the strength of the vibration while the vibration is being provided is equal to or more than a second threshold value.

According to the present disclosure, the controller determines that the driver is in an abnormal state when the average value of the value indicating the strength of the vibration at the excitation frequency while vibration is provided to the steering wheel is equal to or more than the first threshold value and/or the standard deviation of the value indicating the strength of the vibration at the excitation frequency while vibration is being provided is equal to or more than the second threshold value. Therefore, an abnormal state of the driver can be determined with use of a difference in the responsiveness of the muscle in accordance with whether there is disease when vibration is provided to the steering wheel, specifically, with use of the fact that the magnitude and the dispersion of the strength of the detected vibration at the excitation frequency change in accordance with whether there is disease. Therefore, the decline of the physical function of the driver can be detected and the determination of an abnormal state can be confirmed early on in a stage in which a function of voluntary movement declines before the driver becomes unable to drive.

In the present disclosure, the first threshold value is preferably an average value of the value indicating the strength of the detected vibration at the excitation frequency when the vibration is provided to the steering wheel when the steering wheel is not gripped by the driver.

According to the present disclosure, the average value of the value indicating the strength of the vibration at the excitation frequency for a case where there are no influences due to the response characteristics of the muscle of the driver can be set as a reference. When the average value of the value indicating the strength of the vibration at the excitation frequency is smaller than the reference, it can be determined that there is no tension in the muscle of the driver and the vibration is able to be absorbed, in other words, the driver is in a normal state. When the average value of the value indicating the strength of the vibration at the excitation frequency is equal to or more than the reference, it can be determined that there is tension in the muscle of the driver and the vibration is being reflected, in other words, the driver is in an abnormal state.

In the present disclosure, the second threshold is preferably a value that is 20% of the first threshold value.

According to the present disclosure, about 20% of the average value of the value indicating the strength of the vibration at the excitation frequency for a case where there are no influences due to the response characteristics of the muscle of the driver can be set as a reference. When the standard deviation of the value indicating the strength of the vibration at the excitation frequency is smaller than the reference, it can be determined that there are no abnormal movements in the muscle of the driver and a dispersion is suppressed, in other words, the driver is in a normal state. When the standard deviation of the value indicating the strength of the vibration at the excitation frequency is equal to or more than the reference, it can be determined that there is an abnormal movement in the muscle of the driver and a dispersion is occurring, in other words, the driver is in an abnormal state.

In the present disclosure, the vibration detector is preferably a steering torque sensor that detects a steering torque applied to the steering wheel, and the value indicating the strength of the vibration is preferably an effective value of the steering torque at the excitation frequency detected by the steering torque sensor or a decibel value obtained by the effective value of the steering torque being expressed as a level.

According to the present disclosure, the steering torque sensor can be used as the vibration detector without newly providing a vibration detector, and the determination of an abnormal state of the driver can be confirmed early based on a correlation between the time variation of the effective value of the steering torque at the excitation frequency or the time variation of the decibel value obtained by the effective value of the steering torque being expressed as a level and the time variation of the steering angle.

In the present disclosure, a sensor that detects a state of the driver is preferably further included. The controller preferably provides vibration at the excitation frequency to the steering wheel by the vibration apparatus when it is estimated that the driver is in an abnormal state based on a detection signal of the sensor. According to the present disclosure, in a case where a possibility of the driver being in an abnormal state is relatively high based on the detection signal of the sensor, the determination of the abnormal state by providing vibration can be performed, and it can be determined that the driver is in an abnormal state at high accuracy.

In the present disclosure, the vibration apparatus is preferably an electric motor for an electric power steering apparatus for assisting a steering operation of the steering wheel by the driver. According to the present disclosure, the electric motor of the electric power steering apparatus can be used as the vibration apparatus without newly providing a vibration apparatus.

According to the driver state determination apparatus of the present disclosure, it is possible to detect the decline of the physical function of the driver and confirm the determination of an abnormal state sufficiently before the driver becomes unable to drive.

DETAILED DESCRIPTION

Figure 1:
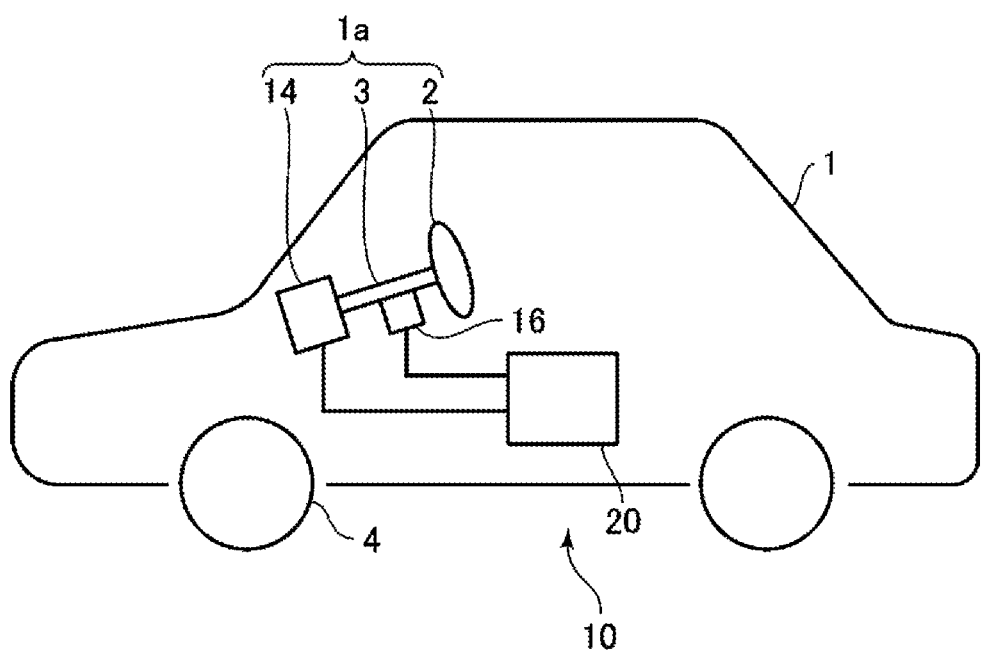
FIG. 1 is an explanatory view of a vehicle on which a driver state determination apparatus according to an embodiment of the present disclosure is mounted.

A driver state determination apparatus according to an embodiment of the present disclosure is described below with reference to the accompanying drawings. FIG. 1 is an explanatory view of a vehicle on which the driver state determination apparatus is mounted, and FIG. 2 is a block diagram of the driver state determination apparatus.

As illustrated in FIG. 1, a driver state determination apparatus 10 according to the embodiment of the present disclosure is mounted on a vehicle 1 having a steering apparatus 1a. The steering apparatus 1a includes a steering wheel 2, a steering shaft 3 fixedly joined thereto, and a joining mechanism (not shown) that joins the steering shaft 3 and the steered wheel 4 to each other.

Figure 2:
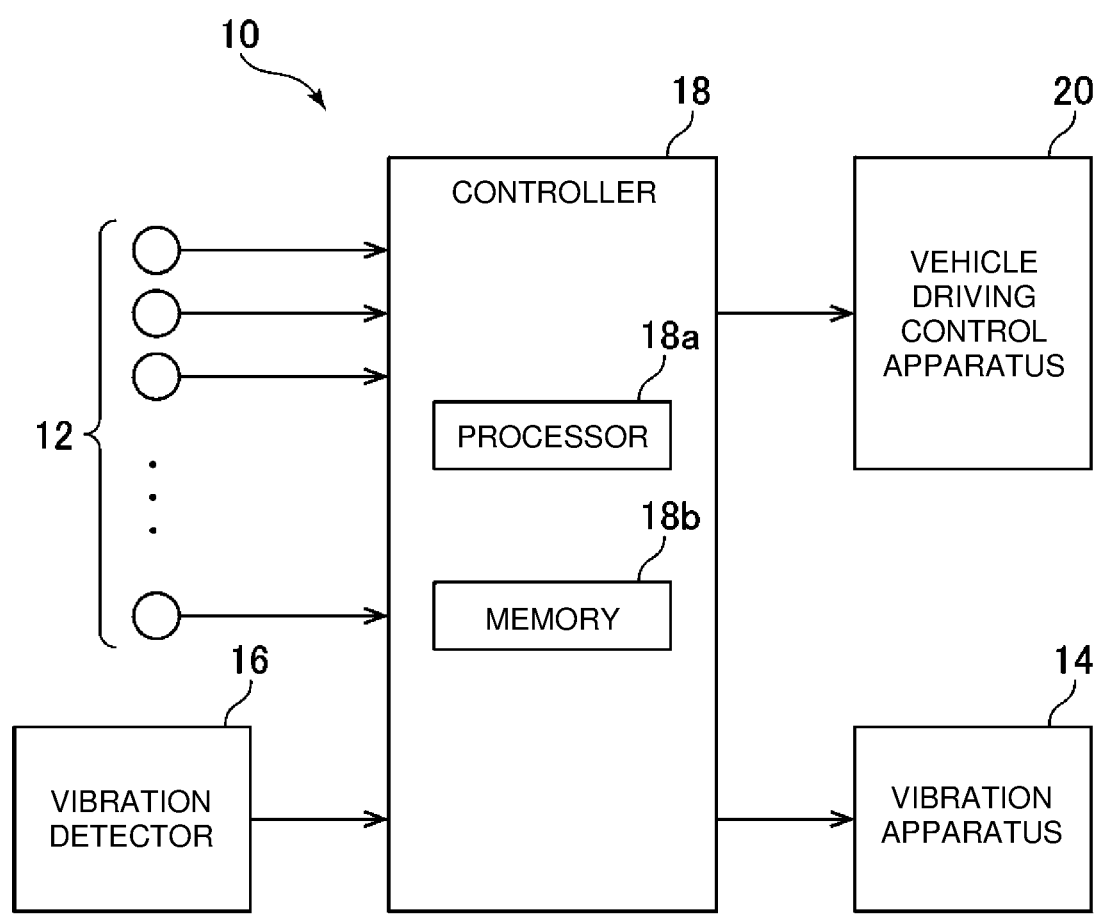
FIG. 2 is a block diagram of the driver state determination apparatus according to the embodiment of the present disclosure.

As illustrated in FIG. 2, the driver state determination apparatus 10 includes one or a plurality of sensors 12 that detect the state of the driver, a vibration apparatus 14 that provides a predetermined vibration to the steering wheel 2, a vibration detector 16 that detects the vibration of the steering wheel 2 or the steering shaft 3, a controller 18, and a vehicle driving control apparatus 20.

The sensors 12 are sensors that detect the state of the driver. The state of the driver includes a physical state of the driver and a vehicle operation state by the driver. The sensors 12 that detect the physical state are an in-vehicle camera that images the driver, a heart rate sensor, an electrocardiogram sensor, and a grip force sensor of the steering wheel 2, for example. The sensors 12 that detect the vehicle operation state are an out-vehicle camera that images the outside of the vehicle, a vehicle speed sensor, an acceleration speed sensor, a yaw rate sensor, a steering angle sensor, a steering torque sensor, an accelerator opening sensor, a brake pressure sensor, a GPS sensor, an ADAS sensor, and the like.

For example, the controller 18 can detect the gaze direction and the posture (the position of the upper body or the head) of the driver, the opening degree of the eyelids of the driver, the grip force of the driver on the steering wheel 2, and the like with use of an imaging signal (image data) of the driver imaged by the in-vehicle camera and estimate that the driver is in an abnormal state based on detection results as above. For example, it can be estimated that the driver is in an abnormal state when the stability of the gaze direction is equal to or less than a predetermined value, when the stability of the posture is equal to or less than a predetermined value, when the eyelids are closed for a predetermined amount of time or more, or when the grip force on the steering wheel 2 is less than a predetermined value. For example, the controller 18 can estimate that the driver is in an abnormal state based on a steering angle signal detected by the steering angle sensor, an image signal imaged by the out-vehicle camera, and the like. For example, it can be estimated that the driver is in an abnormal state when the stability of the position of the vehicle 1 from a centerline on a traveling road, the stability of the steering angle, and the like are equal to or less than a predetermined value.

The vibration apparatus 14 includes an electric motor capable of outputting a reciprocating rotation and is attached to the steering shaft 3. The vibration apparatus 14 is configured to move the steering shaft 3 in a reciprocatively rotating manner in the circumferential direction at a predetermined frequency and a small angle when the vibration apparatus 14 receives a control signal. As a result, vibration at a predetermined frequency is provided to the steering wheel 2 via the steering shaft 3. The vibration detector 16 is attached to the steering shaft 3 and detects the vibration state of the steering wheel 2 via the steering shaft 3.

The vehicle 1 includes an electric power steering apparatus. The electric power steering apparatus includes an electric motor joined to the steering shaft 3 in order to provide a steering assist torque, a steering torque sensor joined to the steering shaft 3 in order to detect a steering torque applied to the steering wheel 2, and the like. In this embodiment, out of components of the electric power steering apparatus, the electric motor configures the vibration apparatus 14, and the steering torque sensor configures the vibration detector 16.

Therefore, the electric motor operates so as to provide an assist torque to the steering shaft 3 as the electric power steering apparatus. The electric motor operates so as to vibrate the steering shaft 3 and the steering wheel 2 by reciprocating the steering shaft 3 in the circumferential direction at a small angle as the vibration apparatus 14.

The steering torque sensor operates so as to detect the steering torque applied to the steering shaft 3 via the steering wheel 2 as the electric power steering apparatus and the vibration detector 16. The steering torque sensor detects the vibration of the steering wheel 2 by detecting the fluctuation of the steering torque in accordance with the torsion of the steering shaft 3 in the circumferential direction. The controller 18 calculates the strength of the vibration of the steering wheel 2 at a predetermined frequency based on time variation of the steering torque detected by the vibration detector 16 (steering torque sensor).

The controller 18 is a computer device including a processor 18a serving as a CPU, a memory 18b (a RAM, a ROM, or the like) that stores therein various programs and databases, an input and output apparatus for electric signals, and the like. The controller 18 controls the sensors 12, the vibration apparatus 14, the vibration detector 16, and the vehicle driving control apparatus 20. The controller 18 is configured to transmit a control signal to the vehicle driving control apparatus 20 and stop the vehicle 1 at a safe place by autonomous driving when the controller 18 determines that the driver is in an abnormal state with use of the sensors 12, the vibration apparatus 14, and the vibration detector 16. The vehicle driving control apparatus 20 is a steering control apparatus, an engine control apparatus, a driving electric motor control apparatus, a brake control apparatus, or the like.

The controller 18 receives a detection signal from the various sensors 12 and estimates whether the physical function of the driver had declined (whether the driver is in an abnormal state) based on the detection signal. When it is estimated that the driver is in an abnormal state, the controller 18 outputs an operation signal to the vibration apparatus 14 for a predetermined period of time (for example, one second) and receives a detection signal from the vibration detector 16. The controller 18 determines whether the driver is in an abnormal state (confirms that the driver is in an abnormal state) based on the detection signal. When it is determined that the driver is in an abnormal state, the controller 18 stops the vehicle 1 by autonomous driving by the vehicle driving control apparatus 20.

Figure 3:
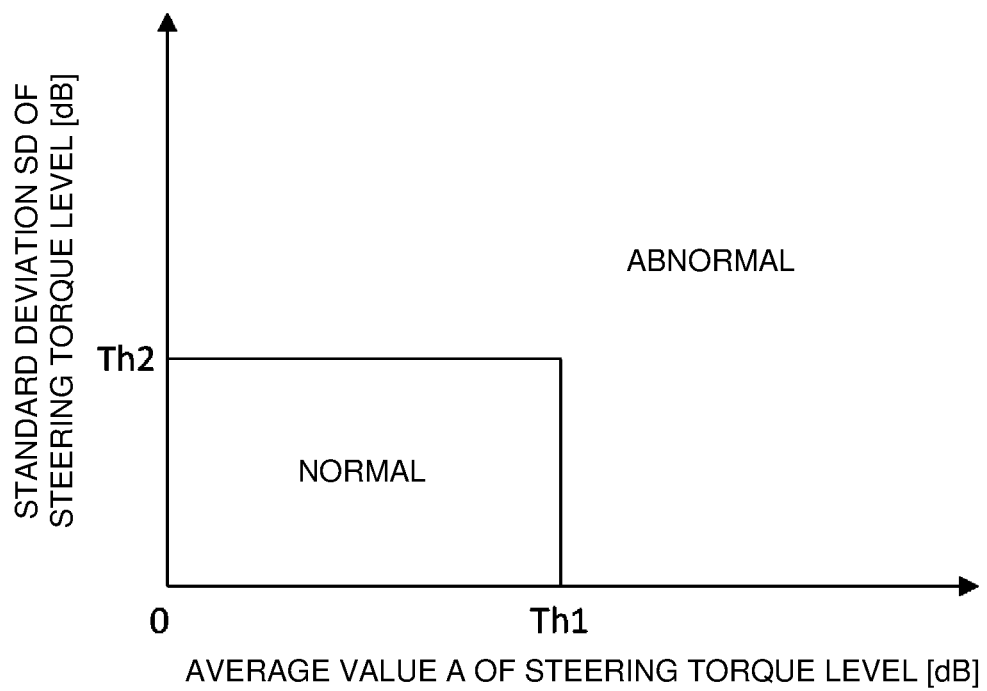
FIG. 3 is a map for determining a driver state based on an average value and a standard deviation of a steering torque level according to the embodiment of the present disclosure.
Figure 4:
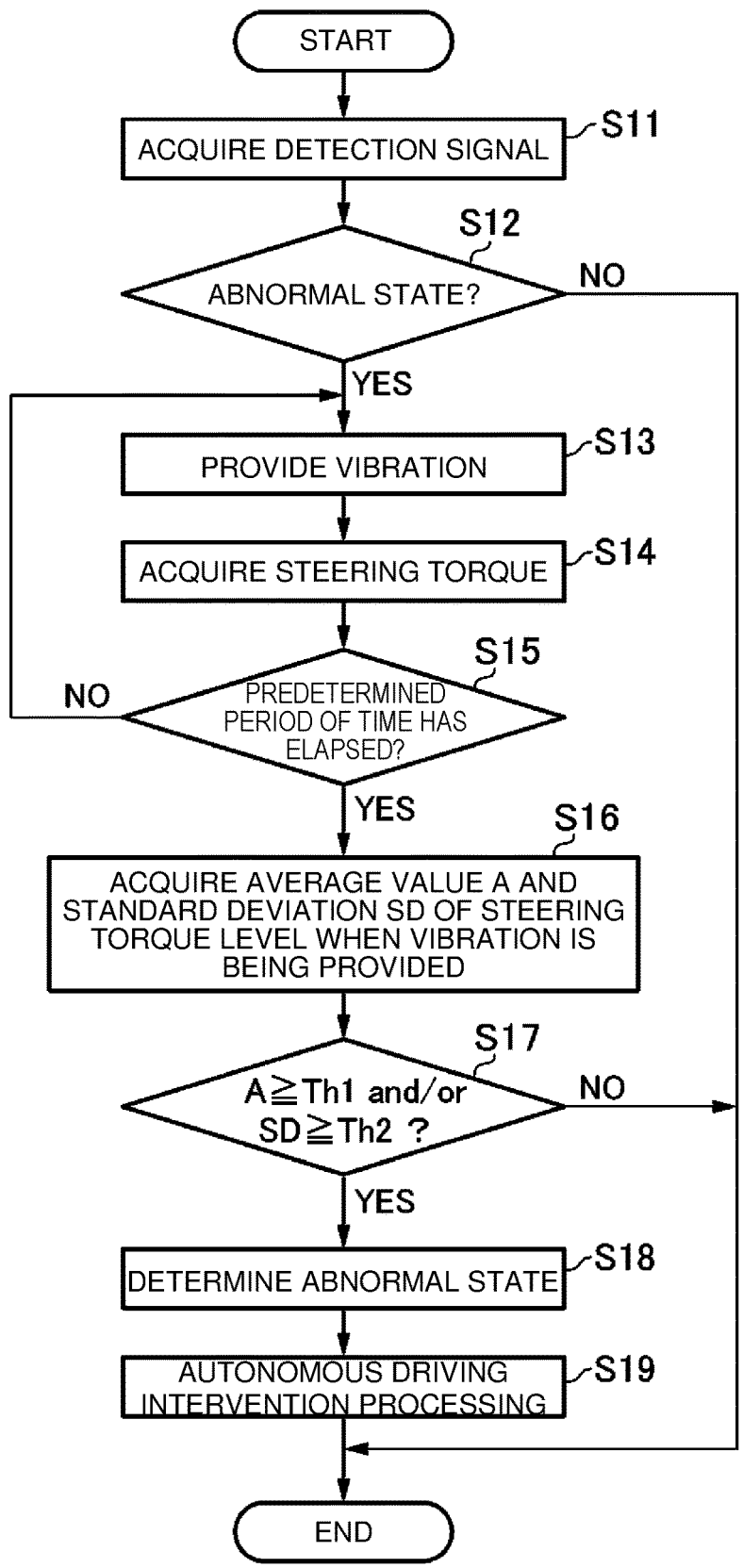
FIG. 4 is a flowchart of processing of determining an abnormal state according to the embodiment of the present disclosure.

Next, processing of determining an abnormal state by the driver state determination apparatus 10 of this embodiment is described with reference to FIG. 3. FIG. 3 is a map for determining a driver state based on an average value and a standard deviation of a steering torque level. The horizontal axis indicates the average value of the steering torque level, and the vertical axis indicates the standard deviation of the steering torque level.

The vibration apparatus 14 provides a vibration at a predetermined frequency (for example, an excitation frequency f0=20 Hz) to the steering wheel 2 for a predetermined period of time. The vibration detector 16 outputs at least a detection signal detected in the predetermined period of time (for example, one second) to the controller 18. The controller 18 performs filter processing of the detection signal that is a time-series signal received from the vibration detector 16 with use of Fourier transform and the like and acquires a time-series signal of the steering torque at the excitation frequency f0. A decibel value (steering torque level [dB]) obtained by an effective value of the steering torque being expressed as a level is calculated from the acquired time-series signal of the steering torque at the excitation frequency f0 as a value indicating the strength of the vibration of the steering wheel 2 at the excitation frequency f0.

It has hitherto been known that an abnormality occurs in muscle tension and coordinated movement when disease (for example, disease of the basal ganglia) related to physical movement occurs. It is also known that viscoelasticity of the muscle changes in accordance with how force is applied to the muscle. Thus, the inventors of the present disclosure have set up a hypothesis as follows. A difference in movement and tension of each muscle for holding the steering wheel occurs between a driver in a normal state and a driver in an abnormal state whose physical function has declined. As a result, a difference occurs in the viscoelasticity of the muscle. Therefore, a difference occurs in response characteristics of the muscle when vibration is input to the muscle of the driver via the steering wheel. As a result of conduction of research by the inventors of the present disclosure based on this hypothesis, it has been experimentally found that a variation (for example, a standard deviation) and a magnitude (for example, an average value) of the strength (for example, the steering torque level) of the detected vibration at the excitation frequency change in accordance with whether there is disease when vibration is provided to the steering wheel.

A map shown in FIG. 3 expresses a region in which the driver is in a normal state and a region in which the driver is in an abnormal state where an average value A [dB] of the steering torque level at the excitation frequency is the horizontal axis and a standard deviation SD [dB] of the steering torque level is the vertical axis when vibration is provided to the steering wheel based on the research result of the inventors of the present disclosure. As illustrated in FIG. 3 here, when the driver is in a normal state, the average value A of the steering torque level at the excitation frequency is less than a first threshold value Th1 and the standard deviation SD of the steering torque level is less than a second threshold value Th2. Meanwhile, when the driver is in an abnormal state, the average value A of the steering torque level at the excitation frequency is equal to or more than the first threshold value Th1 and/or the standard deviation SD of the steering torque level is equal to or more than the second threshold value Th2.

Here, the first threshold value Th1 is an average value of the steering torque level at the excitation frequency when vibration is provided to the steering wheel that is not gripped by the driver. In other words, the average value of the steering torque level for a case where there are no influences due to the response characteristics of the muscle of the driver can be set as a reference. When the average value A of the steering torque level is smaller than the reference, it can be determined that there is no tension in the muscle of the driver and the vibration is able to be absorbed, in other words, the driver is in a normal state. When the average value A of the steering torque level is equal to or more than the reference, it can be determined that there is tension in the muscle of the driver and the vibration is being reflected, in other words, the driver is in an abnormal state.

The second threshold value Th2 is a value that is about 20% of the first threshold value Th1. In other words, about 20% of the average value of the steering torque level for a case where there are no influences due to the response characteristics of the muscle of the driver can be set as a reference. When the standard deviation SD of the steering torque level is smaller than the reference, it can be determined that there are no abnormal movements in the muscle of the driver and a dispersion is suppressed, in other words, the driver is in a normal state. When the standard deviation SD of the steering torque level is equal to or more than the reference, it can be determined that there is an abnormal movement in the muscle of the driver and a dispersion is occurring, in other words, the driver is in an abnormal state.

The first threshold value Th1 and the second threshold value Th2 can be experimentally acquired. The driver state determination apparatus of this embodiment can determine whether the driver is in an abnormal state by providing vibration to the steering wheel 2 and analyzing a reaction thereof with use of the response characteristics of the muscle as those shown in FIG. 3.

Next, the flow of the processing of determining an abnormal state by the driver state determination apparatus 10 of this embodiment is described with reference to FIG. 6. FIG. 6 is a flowchart of the processing of determining an abnormal state.

The abnormal state determination processing in FIG. 6 is started when a power source of the vehicle 1 is turned ON and is repeatedly executed by the controller 18. When the abnormal state determination processing is started, first, the controller 18 acquires a detection signal from the sensor 12 (Step S11) and estimates whether the driver is in a normal state or an abnormal state based on the detection signal (Step S12). The abnormal state determination processing is ended when it is estimated that the driver is not in an abnormal state (in other words, in a normal state) (S12: No) as a result thereof.

Meanwhile, when it is estimated that the driver is in an abnormal state (Step S12: Yes), the controller 18 outputs a control signal and vibrates the steering wheel 2 at a predetermined excitation frequency f0 for a predetermined period of time (for example, one second) by the vibration apparatus 14 (Step S13). When vibration is provided to the steering wheel by the vibration apparatus 14, the controller 18 acquires the steering torque from the vibration detector 16 (steering torque sensor) (Step S14).

When a predetermined period of time elapses (Step S15: Yes), the controller 18 performs filter processing of the time-series signal of the steering torque acquired from the vibration detector 16 and acquires a time-series signal of the steering torque at the excitation frequency f0. A steering torque level obtained by an effective value of the steering torque at the excitation frequency f0 being expressed as a level is calculated from the acquired time-series signal of the steering torque at the excitation frequency f0. Then, the average value A and the standard deviation SD of the steering torque level at the excitation frequency f0 while vibration is being provided is calculated (Step S16).

When the calculated average value A of the steering torque level at the excitation frequency f0 is less than the first threshold value Th1 and the standard deviation SD of the steering torque level at the excitation frequency f0 is less than the second threshold value Th2 (Step S17: No), the controller 18 determines that the driver is not in an abnormal state and ends the abnormal state determination processing.

Meanwhile, when the average value A of the steering torque level at the excitation frequency f0 calculated in Step S16 is equal to or more than the first threshold value Th1 and/or the standard deviation SD of the steering torque level at the excitation frequency f0 calculated in Step S16 is equal to or more than the second threshold value Th2 (Step S17: Yes), the controller 18 determines that the driver is in an abnormal state (Step S18) and executes autonomous driving intervention processing (Step S19). In the autonomous driving intervention processing, the controller 18 sends out a control signal to the vehicle driving control apparatus 20 and stops the vehicle 1 at a safe place by autonomous driving, for example. After Step S19, the controller 18 ends the abnormal state determination processing.

In this embodiment, when an abnormal state of the driver is estimated in the processing in Step S12 (Step S12: Yes), vibration is provided to the steering wheel 2 (Step S13). However, the determination of the abnormal state (Steps S16, S17) may be performed by regularly providing vibration to the steering wheel 2 besides the processing in Step S12.

In this embodiment, a decibel value (steering torque level) obtained by an effective value of the steering torque being expressed as a level is used as the value indicating the strength of the vibration of the steering wheel 2 at the excitation frequency f0. However, an effective value of the steering torque may be used, and an abnormal state of the driver may be determined based on the average value and the standard deviation of the effective value of the steering torque at the excitation frequency f0.

Next, working effects of the driver state determination apparatus 10 of this embodiment described above are described.

The controller 18 provides vibration at the predetermined excitation frequency f0 to the steering wheel 2 by the vibration apparatus 14, calculates a value indicating the steering torque level at the predetermined excitation frequency f0 based on the vibration detected by the vibration detector 16, and determines that the driver is in an abnormal state when the average value A of the steering torque level while the vibration is being provided is equal to or more than the first threshold value Th1 and/or the standard deviation SD of the steering torque level while the vibration is being provided is equal to or more than the second threshold value Th2. As a result, an abnormal state of the driver can be determined with use of a difference in the responsiveness of the muscle in accordance with whether there is disease when vibration is provided to the steering wheel 2, specifically, with use of the fact that the magnitude and the dispersion of the strength of the detected vibration at the excitation frequency change in accordance with whether there is disease. Therefore, the decline of the physical function of the driver can be detected and the determination of an abnormal state can be confirmed early on in a stage in which the function of voluntary movement declines before the driver becomes unable to drive.

The first threshold value Th1 is the average value of the steering torque level at the excitation frequency f0 when vibration is provided to the steering wheel 2 that is not gripped by the driver. As a result, the average value of the steering torque level for a case where there are no influences due to the response characteristics of the muscle of the driver can be set as a reference. When the average value A of the steering torque level is smaller than the reference, it can be determined that there is no tension in the muscle of the driver and the vibration is able to be absorbed, the driver is in a normal state. When the average value A of the steering torque level is equal to or more than the reference, it can be determined that there is tension in the muscle of the driver and the vibration is being reflected, in other words, the driver is in an abnormal state.

The second threshold value Th2 is a value that is 20% of the first threshold value Th1. As a result, about 20% of the average value of the steering torque level for a case where there are no influences due to the response characteristics of the muscle of the driver can be set as a reference. When the standard deviation SD of the steering torque level is smaller than the reference, it can be determined that there are no abnormal movements in the muscle of the driver and a dispersion is suppressed, in other words, the driver is in a normal state. When the standard deviation SD of the steering torque level is equal to or more than the reference, it can be determined that there is an abnormal movement in the muscle of the driver and a dispersion is occurring, in other words, the driver is in an abnormal state.

The vibration detector 16 is a steering torque sensor that detects the steering torque applied to the steering wheel 2, and the value indicating the strength of the vibration is an effective value of the steering torque at the excitation frequency f0 detected by the steering torque sensor or a decibel value obtained by the effective value of the steering torque being expressed as a level. As a result, the steering torque sensor can be used as the vibration detector 16 without newly providing the vibration detector 16, and the determination of an abnormal state of the driver can be confirmed early based on the average value and the standard deviation of the effective value of the steering torque at the excitation frequency f0 or the decibel value obtained by the effective value of the steering torque being expressed as a level.

The controller 18 provides vibration at the predetermined excitation frequency f0 to the steering wheel 2 by the vibration apparatus 14 when it is estimated that the driver is in an abnormal state based on a detection signal of the sensor 12. As a result, in a case where a possibility of the driver being in an abnormal state is relatively high based on the detection signal of the sensor 12, the determination of an abnormal state by providing vibration can be performed, and it can be determined that the driver is in an abnormal state at high accuracy.

The vibration apparatus 14 is an electric motor for an electric power steering apparatus for assisting the steering operation of the steering wheel 2 by the driver. As a result, the electric motor of the electric power steering apparatus can be used as the vibration apparatus 14 without newly providing the vibration apparatus 14.

What is claimed is:

1. A driver state determination apparatus that determines an abnormal state of a driver that drives a vehicle, the driver state determination apparatus comprising:
    a vibration apparatus that vibrates a steering wheel of a steering apparatus of the vehicle;
    a vibration detector that detects a vibration of the steering wheel; and
    a controller that controls the vibration apparatus, wherein the controller is configured to
    provide vibration at a predetermined excitation frequency to the steering wheel by the vibration apparatus,
    calculate, based on the vibration detected by the vibration detector, a value indicating a strength of the detected vibration at the excitation frequency, and
    determine that the driver is in an abnormal state when an average value of the value indicating the strength of the vibration while the vibration is being provided is equal to or more than a first threshold value, and/or a standard deviation of the value indicating the strength of the vibration while the vibration is being provided is equal to or more than a second threshold value.

2. The driver state determination apparatus according to claim 1, wherein the first threshold value is an average value of the value indicating the strength of the detected vibration at the excitation frequency when the vibration is provided to the steering wheel when the steering wheel is not gripped by the driver.

3. The driver state determination apparatus according to claim 2, wherein the second threshold value is a value that is 20% of the first threshold value.

4. The driver state determination apparatus according to claim 3, wherein:
    the vibration detector is a steering torque sensor that detects a steering torque applied to the steering wheel; and
    the value indicating the strength of the vibration is an effective value of the steering torque at the excitation frequency detected by the steering torque sensor or a decibel value obtained by the effective value of the steering torque being expressed as a level.

5. The driver state determination apparatus according to claim 3, further comprising a sensor that detects a state of the driver, wherein
    the controller provides vibration at the excitation frequency to the steering wheel by the vibration apparatus when it is estimated that the driver is in an abnormal state based on a detection signal of the sensor.

6. The driver state determination apparatus according to claim 3, wherein the vibration apparatus is an electric motor for an electric power steering apparatus for assisting a steering operation of the steering wheel by the driver.

7. The driver state determination apparatus according to claim 1, wherein:
    the vibration detector is a steering torque sensor that detects a steering torque applied to the steering wheel; and
    the value indicating the strength of the vibration is an effective value of the steering torque at the excitation frequency detected by the steering torque sensor or a decibel value obtained by the effective value of the steering torque being expressed as a level.

8. The driver state determination apparatus according to claim 1, further comprising a sensor that detects a state of the driver, wherein
    the controller provides vibration at the excitation frequency to the steering wheel by the vibration apparatus when it is estimated that the driver is in an abnormal state based on a detection signal of the sensor.

9. The driver state determination apparatus according to claim 1, wherein the vibration apparatus is an electric motor for an electric power steering apparatus for assisting a steering operation of the steering wheel by the driver.

10. The driver state determination apparatus according to claim 2, wherein:
    the vibration detector is a steering torque sensor that detects a steering torque applied to the steering wheel; and
    the value indicating the strength of the vibration is an effective value of the steering torque at the excitation frequency detected by the steering torque sensor or a decibel value obtained by the effective value of the steering torque being expressed as a level.

11. The driver state determination apparatus according to claim 2, further comprising a sensor that detects a state of the driver, wherein the controller provides vibration at the excitation frequency to the steering wheel by the vibration apparatus when it is estimated that the driver is in an abnormal state based on a detection signal of the sensor.

12. The driver state determination apparatus according to claim 2, wherein the vibration apparatus is an electric motor for an electric power steering apparatus for assisting a steering operation of the steering wheel by the driver.

* * * * *